United States Patent
Warren et al.

(10) Patent No.: US 10,087,235 B2
(45) Date of Patent: Oct. 2, 2018

(54) CONTAMINANT REMOVAL METHOD

(71) Applicant: CSL Limited, Parkville, Victoria (AU)

(72) Inventors: Gary Lee Warren, Bourbonnais, IL (US); Yvonne Vucica, Bern (CH); Christoph Kempf, Detligen (CH); Martin Stucki, Laupen (CH)

(73) Assignee: CSL LIMITED, Parkville, Victoria (AU)

( * ) Notice: Subject to any disclaimer, the term of this patent is extended or adjusted under 35 U.S.C. 154(b) by 0 days.

(21) Appl. No.: 14/910,424

(22) PCT Filed: Aug. 8, 2014

(86) PCT No.: PCT/AU2014/000790
§ 371 (c)(1),
(2) Date: Feb. 5, 2016

(87) PCT Pub. No.: WO2015/017888
PCT Pub. Date: Feb. 12, 2015

(65) Prior Publication Data
US 2016/0176947 A1    Jun. 23, 2016

(30) Foreign Application Priority Data
Aug. 8, 2013 (EP) .................................. 13179755

(51) Int. Cl.
*A61K 38/00* (2006.01)
*C07K 14/775* (2006.01)
*C07K 1/34* (2006.01)

(52) U.S. Cl.
CPC .............. *C07K 14/775* (2013.01); *C07K 1/34* (2013.01); *A61K 38/00* (2013.01)

(58) Field of Classification Search
CPC ......... A61K 38/00; C07K 14/775; C07K 1/34
See application file for complete search history.

(56) References Cited

U.S. PATENT DOCUMENTS

| | | | |
|---|---|---|---|
| 5,089,602 A | 2/1992 | Isliker et al. | |
| 5,652,339 A * | 7/1997 | Lerch ................... | A61K 9/1275 530/359 |
| 6,090,921 A * | 7/2000 | Winge .................. | C07K 14/775 530/359 |
| 6,423,830 B1 * | 7/2002 | Winge .................. | C07K 14/755 530/359 |
| 8,436,152 B2 * | 5/2013 | Brinkman ............. | C07K 14/775 530/380 |
| 8,653,245 B2 | 2/2014 | Brinkman et al. | |
| 8,962,802 B2 * | 2/2015 | Brinkman ............. | C07K 14/775 530/350 |
| 8,999,920 B2 | 4/2015 | Wright et al. | |
| 9,125,943 B2 | 9/2015 | Vucica et al. | |
| 9,187,551 B2 * | 11/2015 | Dasseux .............. | C07K 14/775 |
| 2003/0232969 A1 | 12/2003 | Lengsfeld et al. | |
| 2011/0087008 A1 * | 4/2011 | Brinkman ............ | C07K 14/775 530/359 |
| 2011/0178029 A1 * | 7/2011 | Knudsen .............. | C07K 14/775 514/21.2 |

FOREIGN PATENT DOCUMENTS

| | | |
|---|---|---|
| JP | H01-294699 A | 11/1989 |
| WO | WO 96/00237 A1 | 1/1996 |
| WO | WO 03/105989 A1 | 12/2003 |
| WO | WO 2009/025754 A2 | 2/2009 |
| WO | WO 2009/036460 A2 | 3/2009 |
| WO | WO 2012/000048 A1 | 1/2012 |
| WO | WO 2014/194362 A1 | 9/2015 |

OTHER PUBLICATIONS

Kim et al. Manufacturing and Shelf Stability of Reconstituted High-density Lipoprotein for Infusion Therapy. Biotechnology and Bioprocess Engineering, 2011. vol. 16, pp. 785-792. (Year: 2011).*
U.S. Appl. No. 14/893,178, filed Nov. 23, 2015, Vucica et al.
Aranha-Creado et al., "Clearance of murine leukaemia virus from monoclonal antibody solution by a hydrophilic PVDF microporous membrane filter." Biologicals, 1998; 26(2): 167-72.
Brandwein and Aranha-Creado, "Membrane filtration for virus removal." Dev Biol (Basel), 1999; 102: 157-63.
Burnouf and Radosevich, "Nanofiltration of plasma-derived biopharmaceutical products." Haemophilia, Jan. 2003; 9(1): 24-37.
Burnouf, "Value of virus filtration as a method for improving the safety of plasma products." Vox Sang, 1996; 70(4): 235-6.
Contiero et al., "Apolipoprotein AI isoforms in serum determined by isoelectric focusing and immunoblotting." Electrophoresis, 1997; 18(1): 122-6.
Edelstein et al., "Effect of Guanidine Hydrochloride on the Hydrodynamic and Thermodynamic Properties of human Apolipoprotein A-1 in Solution," JBC, Jun. 1980; 255(12): 5747-54.
Edelstein, "Isolation and Characterization of a Dog Serum Lipoprotein Having Apolipoprotein A-1 as Its Predominant Protein Constituent," Biochem, 1976; 15(9): 1934-41.
Hénin et al., "Inactivation and partition of human immunodeficiency virus during Kistler and Nitschmann fractionation of human blood plasma." Vox Sang, 1988; 54(2): 78-83.
Kim, "Manufacturing and Shelf Stability of Reconstituted High-density Lipoprotein for Infusion Therapy," Biotech Bioprocess Eng. Aug. 2011; 16: 785-92.
Lerch et al, "Production and characterization of a reconstituted high density lipoprotein for therapeutic applications." Vox Sang, Sep. 1996; 71(3): 155-64.

(Continued)

*Primary Examiner* — Marcela M Cordero Garcia
(74) *Attorney, Agent, or Firm* — Foley & Lardner LLP

(57) ABSTRACT

A method for purifying Apo A-I is provided including the steps of providing a solution comprising Apo A-I and guanidine hydrochloride and filtering the solution through a filter having a pore size in a range from 15 nm to 35 nm to thereby reduce viral contamination of the Apo A-I. An Apo A-I preparation is provided having at least a 12 log LRV (log reduction value) for a parvovirus; and/or at least 9 log LRV for a non-enveloped virus; and/or at least 8.5 log LRV for a lipid enveloped virus. Also provided are pharmaceutical compositions and reconstituted high density lipoprotein formulation comprising Apo A-I and methods of treating diseases disorders or conditions.

13 Claims, 4 Drawing Sheets

(56) References Cited

OTHER PUBLICATIONS

Lund-Katz and Phillips, "High density lipoprotein structure-function and role in reverse cholesterol transport." *Subcell Biochem*, 2010; 51: 183-227.

Manabe. "Removal of virus through novel membrane filtration method." *Dev Biol Stand*, 1996; 88: 81 90.

Mocé-Livina et al., "Comparison of polyvinylidene fluoride and polyether sulfone membranes in filtering viral suspensions." *J Virol Methods*, 2003; 109(1): 99-101.

Schlegel et al.. "Virus inactivation of plasma-derived proteins by pasteurization in the presence of guanidine hydrochloride." *Transfusion*, 2001, 41(3): 382-9.

Suurkuusk and Hallén, "Investigation of guanidine hydrochloride induced unfolding of apolipoprotein A-I $_{Milano}$." *Spectroscopy*, 2002; 16(3-4): 199-206.

European Search Report dated Jan. 2, 2014 in application No. EP 13179755.

International Search Report dated Oct. 29, 2014 in application No. PCT/AU2014/000790.

AsahiKASEI, "Planova BioEX," BioEX Medical Manufacturing Product, Retrieved from the internet; URL https://web.archive.org/web/2013017083545/http://www.asahi-kasei.co.jp:80/medical/manufacturinq/product/bioex/ (Jul. 2013). Searched on May 22, 2018.

* cited by examiner

CONTAMINANT REMOVAL METHOD

TECHNICAL FIELD

The invention relates to a method for purifying apolipoprotein, in particular for removing viral pathogens from apolipoprotein A-I (Apo A-I) containing solutions and to provide an Apo A-I preparation.

BACKGROUND

Apolipoproteins are the major protein component in soluble lipoprotein complexes with apolipoprotein A-I (Apo A-I) being the major protein component in high density lipoprotein (HDL) particles.

The apolipoproteins of the A, C and E families have evolved from a common ancestral gene and are structurally similar. These protein molecules generally contain a series of 22-amino acid tandem repeats that are often separated by proline residues. The repeating 22-amino acid segments form amphipathic α-helices which enable binding to both lipid and water surfaces. In the case of human Apo A-I (243 amino acids; 28.1 kDa) there are eight 22-mer and two 11-mer amphipathic helices (Lund-Katz & Phillips, 2010, Subcell Biochem. 51, 183-227). The amphipathic α-helices of the apolipoproteins play a critical role in stabilising the lipoprotein. They do this by orientating the apolipoprotein so that the predominantly hydrophobic helical faces can interact with the hydrophobic lipids in the complex whilst the opposing predominantly hydrophilic faces of the apolipoprotein interact with the surrounding aqueous environment. However when these proteins are separated from the lipid component, exposure of the hydrophobic amino acid residues to an aqueous environment can make them difficult to handle. In particular the hydrophobic faces of the α-helices have a tendency to self-associate resulting in aggregate formation and in some conditions precipitation. For example, a 1 mg/mL solution containing Apo A-I Milano is estimated to contain 80% of the protein in an aggregated form when stored in 50 mM phosphate buffer at pH 7.4 (Suurkuust & Hallen, 2002, Spectroscopy 16, 199-206).

Apo A-I is synthesized by the liver and intestine and is responsible for the physiological function of HDL in the blood; the removal of cholesterol from peripheral tissues, carrying it back either to the liver or to other lipoproteins, by a mechanism known as "reverse cholesterol transport" (RCT). As a consequence the HDL particles are present in plasma in a range of sizes and are continually remodelling due to these RCT lipid transfer activities. Thus HDL particles are characterized by a high density (>1.063 g/ml) and sizes ranging from about 5 to 20 nm (Stoke's diameter). The clear correlation between elevated levels of serum cholesterol and the development of coronary heart disease (CHD) has been repeatedly confirmed, based on epidemiological and longitudinal studies. Hence, Apo A-I in HDL is thought to have an anti-inflammatory function and to restrain the occurrence and development of CHD. Furthermore, Apo A-I has shown to decrease the Low Density Lipoproteins (LDL) level in the blood and is known to bind to lipopolysaccharides or endotoxins, thus having a major role in the anti-endotoxin function of HDL. The "protective" role of HDL and Apo A-I as the primary protein constituent has been confirmed in a number of studies. High plasma levels of Apo A-I are associated with a reduced risk of CHD and presence of coronary lesions. Apo A-I is thus promising for applications in drugs like reconstituted HDL for applications in acute coronary syndromes, atherosclerosis treatment, anti-inflammation treatment, antitoxin treatment, liver-targeting drugs, etc.

Biological therapeutics of either recombinant or plasma origin are commonly manufactured using biological feedstocks that are intrinsically contaminated with pathogens such as viruses. Moreover, some manufacturing processes are, by their nature, susceptible to pathogen contamination from extrinsic sources. Accordingly, manufacturers of biological therapeutics are required to incorporate sufficient virus clearance steps into their manufacturing processes to ensure that their products are contaminant-free.

Biotechnology products (typically proteins or DNA) are produced with recombinant DNA in cell cultures, transgenic animals, or transgenic plants. Common cells used for production include Chinese Hamster Ovary (CHO) cells, E. coli bacteria, and yeast. Cell-based production systems are typically carried out in batch mode although a small number of perfusion systems are also in use. Final commercial scale fermentation is carried out at 1,000-100,000 L scale with the majority of CHO based fermenters in the 8,000-25,000 L scale.

Human blood plasma is nowadays collected in large amounts (for example, it has been estimated that in 2010 that 30 million liters of plasma were collected worldwide) and processed to individual fractions; some of these fractions contain the apolipoprotein, Apo A-I. Examples of such plasma fractions include Cohn Supernatant I, Cohn Fraction II+III, and Cohn Fraction IV (e.g. Cohn Fraction IV-1) or variations thereof (e.g. is a Kistler/Nitschmann Fraction IV). Since blood and plasma potentially contain transfusion-transmissible pathogens, such pathogens, in particular viruses must be removed or inactivated when blood- or plasma-derived components are used as therapeutics or as a vehicle for therapeutic delivery. However, viruses are often not easily removed and may still be present in plasma-derived components, even if they are highly purified. In particular, small non-enveloped viruses such as Picomaviridae (e.g. hepatitis A virus) which have a size of about 27-32 nm and Parvoviruses which have a size of about 18-26 nm, are of special concern. This is due to both their small size and their high physiochemical stability. Thus, there is an ongoing need for the development of methods that allow for efficient virus removal or inactivation of plasma-derived protein therapeutics.

Common virus inactivation technologies include physical methods such as the classical pasteurization procedure (60° C. heating for 10 hours), short wavelength ultra-violet light irradiation, or gamma irradiation and chemical methods such as solvent detergent or low pH incubation. Virus removal technologies include size exclusion methods such as virus filtration which is also often referred to as nanofiltration. These virus filtration methods have been shown to be effective methods for removing viruses from protein solutions.

Virus filtration has the benefit of being a mild method for removing viruses from protein solutions, and generally allows for a high level of protein recovery and the biological activity of the proteins to be fully preserved. Optimal virus filters must maximize capacity, throughput, and selectivity. The capacity of a virus filter is the total volume of filtrate per $m^2$ of filter surface area that can be processed before the flux declines to an unacceptably low value during constant pressure filtration. Throughput refers to the speed at which the feed can be filtered (maximum sustainable permeate flux). Selectivity refers to the ability to yield high product recovery and high virus particle retention. These filters must be able to process the entire bulk feed at acceptable filtrate fluxes, reject virus particles, and maximize protein passage. Fouling during virus filtration is typically dominated by protein aggregates, DNA, partially denatured product, or other debris.

Filter manufacturers often assign terms like nominal or mean pore size ratings to commercial filters, which usually indicate meeting certain retention criteria for particles or microorganisms rather than the geometrical size of the actual pores.

For viral clearance, filtration is conducted through a filter membrane, which has a nominal pore size smaller than the effective diameter of the virus which is to be removed. The presence of only a small number of abnormally large pores (300 kDa or larger nominal molecular weight cutoff, NMWCO) will permit excessive virus leakage. Hence virus filters must be manufactured so as to eliminate all macro-defects. This is typically accomplished through the use of composite membranes that provide the required combination of virus retention and mechanical stability. Virus-removing filter membranes are typically made from materials such as regenerated cellulose, for example a cuprammonium-regenerated cellulose or synthetic polymer materials like hydrophilic polyvinylidene fluoride (PVDF) or hydrophilic polyether-sulfone (PES) as described in the literature: Manabe. S, Removal of virus through novel membrane filtration method, Dev. Biol. Stand, (1996) 88: 81-90; Brandwein H et al., Membrane filtration for virus removal, Dev Biol (Basel), (2000) 102: 157-63; Aranha-Creado et al., Clearance of murine leukaemia virus from monoclonal antibody solution by a hydrophilic PVDF microporous membrane filter, Biologicals. (1998) June; 26 (2): 167-72; Mocé-Llivina et al., Comparison of polyvinylidene fluoride and polyether sulfone membranes in filtering viral suspensions, Journal of Virological Methods, (2003) April, Vol. 109, Issue 1, Pages 99-101.

Virus filtration methods that have been described include WO96/00237 which relates to a method of virus-filtering a solution that contains macromolecules (i.e. protein) by adding salt to the solution to a level of at least 0.2 M. The applicants recommend using salts that exhibit the high salting-out effect that is characteristic of the high end of the Hofmeister series, in particular citrate, tartrate, sulfate, acetate or phosphate anions and sodium, potassium, ammonium or calcium cations. Sodium chloride is particularly preferred, and salts that exhibit a low salting-out effect at the low end of the series (e.g. GuHCl) are not used.

Consistent with WO96/00237, Kim et al (Biotechnology & Bioprocess Engineering, 2011, 16, 785-792) describe the virus filtration of Apo A-I in the presence of sodium chloride (250 mM NaCl, 30 mM Tris at pH 8). This step is carried out immediately after elution from a DEAE-FF column. The propensity for Apo A-I to aggregate however imposes a manufacturing limitation in that the filtration step ideally needs to be completed either as the Apo A-I is eluted from the column or alternatively the Apo A-I needs to be stored in the presence of salt at very low protein concentrations (e.g. 0.1 mg/mL). This later approach has the disadvantage of then requiring overly large filtration volumes. The cost of virus filters is substantial. Thus any reduction in filter capacity due to for example apolipoprotein aggregation or overly large filtration volumes can result in significantly higher processing costs at commercial scale.

WO03/105989 relates to the use of clathyrate modifiers such as polyol sugar or sugar alcohol (i.e. sucrose and sorbitol) and is aimed at increasing the hydrophobicity of the filter membrane surface and decreasing the hydrodynamic radius of the protein as well as reducing the tendency for the self-association of the protein desired to be filtered.

US 2003/232969 A1 relates to a method for removing viruses from solutions of high molecular weight proteins like fibrinogen (340 kDa) by nanofiltration.

Apolipoproteins like Apo A-I being relatively small (28 kDa) should be readily amenable to virus filtration. However as already described above their hydrophobic nature along with their unfortunate tendency to form aggregates promote the formation of protein clusters on the filter surface and also to clogging the pores of the filter. In terms of the filter itself, this can occur on the upper surface of the membrane, both by pore blockage and/or by the formation of a cake or deposit, and also within the membrane pore structure. Fouling causes decay in flow rate for constant pressure operation and increases the pressure for operation at constant filtrate flux. As a result of filter fouling there can be reductions to the selectivity of the filtration resulting in lower protein recoveries and/or lower virus retention. Additionally filter fouling reduces the capacity and throughput resulting in longer filtration times and/or the requirement for increased filter area. In addition, operating conditions which are optimal for maintaining apolipoprotein solubility and preventing aggregation might not be optimal for ensuring a high viral clearance. In particular chaotrophic substances that might be used to stabilise the apolipoprotein may alter the filterability properties of the pathogen (e.g. virus) and possibly also the filter membrane. As a consequence, the presence of a chaotrophic substance at particular concentrations might also allow unwanted virus penetration across the filter membrane, thus negating the usefulness of the step for processing solutions comprising apolipoproteins.

It is therefore an object of the present invention to provide a filtration method for safely removing viruses, in particular small non-enveloped viruses such as parvoviridae, which is suitable for solutions comprising apolipoproteins, like Apo A-I, and which is also suitable for industrial application.

SUMMARY

This object is broadly achieved by a method for purifying apolipoprotein A-I (Apo A-I), that comprises the filtering a solution comprising Apo A-I and guanidine hydrochloride (GuHCl) through a filter having a suitable pore size.

According to an aspect of the present invention, there is provided a method for purifying apolipoprotein A-I (Apo A-I), comprising the steps of: a) providing a solution comprising Apo A-I and guanidine hydrochloride (GuHCl); and b) filtering the solution through a filter having a pore size in a range from 15 nm to 35 nm.

In an embodiment, the method is for reducing viral contamination of the Apo A-I. In some embodiments of the invention, the method is for reducing viral contamination of the Apo A-I wherein the viral contamination comprises a parvo virus. In particular embodiments the parvo virus is minute virus of mice (MVM). In some embodiments of the invention, the method is for reducing viral contamination of the Apo A-I wherein the viral contamination comprises a picornaviridae virus. In particular embodiments the picornaviridae virus is encephalomyocarditis (EMCV) or hepatitis A.

In a preferred embodiment, the solution comprises an Apo A-I protein concentration within a range from 5 to 30 g/L, particularly from 5 to 20 g/L, for example 7 to 12 g/L.

In a preferred embodiment, the solution comprises a GuHCl concentration that reduces or inhibits aggregation of the Apo A-I. The solution may in particular comprise a GuHCl concentration within a range from 1.3 to 3.2 M, particularly from 1.5 to 2.0 M. More preferably the GuHCl concentration in the solution is 1.7 M.

In an embodiment, the pH of the solution is within a range from 7.1 to 7.5, such as at 7.3.

In an embodiment, the solution is prepared by one or more steps of: 1) suspending Apo A-I precipitate in 4.0 to 4.6 M GuHCl; and/or 2) diluting the suspension to an Apo A-I protein concentration within a range from 5 to 30 g/L, and/or to a GuHCl concentration within a range from 1.3 M to 3.2 M.

In an embodiment, after step b), a heat treatment step is performed for virus inactivation. The heat treatment may comprise the steps of: adjusting the pH of the solution within a range from 6.6 to 8.0; and subsequently heating the solution at a temperature of 55 to 61° C. for about 30 minutes to about 4 hours.

In an alternative embodiment, prior to step a), a heat treatment step is performed for virus inactivation. The heat treatment may comprise the steps of: providing a solution comprising GuHCl and Apo A-I at a pH within a range from 6.6 to 8.0; and subsequently heating the solution at a temperature of 55 to 61° C. for about 30 minutes to about 4 hours.

In preferred embodiments the solution with a pH within the range from 6.6 to 8.0 comprises a GuHCl concentration within a range from 2.7 to 3.9 M, or more preferably 3.5 M.

In embodiments of the invention, the pH of the solution with a pH within the range from 6.6 to 8.0 is preferably within a range from 7.0 to 8.0. In particular embodiments the pH is 7.3.

An aspect of the present invention also provides Apo A-I purified by the method of the invention.

An aspect of the present invention also provides an Apo A-I preparation with at least 12 log LRV (log reduction value) for a parvovirus; and/or at least 9 log LRV for a non-enveloped virus; and/or at least 8.5 log LRV for a lipid enveloped virus. In particular embodiments the Apo A-I preparation is suitable for pharmaceutical use.

In another aspect, the present invention provides a pharmaceutical composition comprising Apo A-I or the Apo-Al preparation according to the aforementioned aspects together with a pharmaceutically acceptable carrier, diluent or excipient.

In yet another aspect, the invention provides a method of producing a pharmaceutical composition including producing Apo A-I according to the method of the aforementioned aspect and combining the Apo A-I with a pharmaceutically acceptable carrier or diluent; or combining the Apo A-I preparation of the aforementioned aspect with a pharmaceutically acceptable carrier or diluent; to thereby produce the pharmaceutical composition.

A further aspect of the invention provides an rHDL formulation comprising Apo A-I or the Apo-Al preparation according to the aforementioned aspects together with a lipid.

In another further aspect, the invention provides a method of producing a reconstituted HDL formulation including producing Apo A-I according to the method of the aforementioned aspect and combining the Apo A-1 with a lipid; or combining the Apo A-I preparation of the aforementioned aspect with a lipid; to thereby produce the reconstituted HDL formulation.

A yet further aspect of the invention provides a method of treating or preventing a disease, disorder or condition in a mammal including the step of administering to the mammal Apo-A1, an Apo-A1 preparation, a pharmaceutical composition or a rHDL formulation according to any of the aforementioned aspects to a mammal to thereby treat or prevent the disease, disorder or condition.

DETAILED DESCRIPTION

Figure 1:
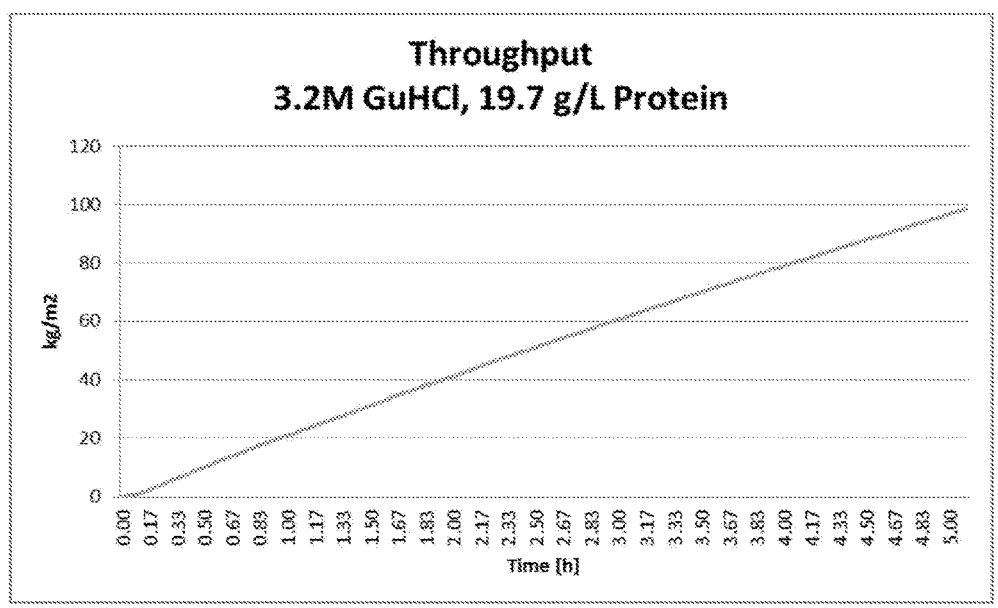
FIG. 1: showing through-put of the solution [kg/m$^2$] during nanofiltration with conditions of 3.2 M GuHCl, 19.7 g/L Protein.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It must be noted that, as used in the subject specification, the singular forms "a", "an" and "the" include plural aspects unless the context clearly dictates otherwise. Thus, for example, reference to "a protein" includes a single protein, as well as two or more proteins.

The term "about" in relation to a numerical value x means, for example, x±10%.

Where the invention provides a process involving multiple sequential steps, the invention can also provide a process involving less than the total number of steps. The different steps can be performed at very different times by different people in different places (e.g. in different countries).

Unless specifically stated, a process comprising a step of mixing two or more components does not require any specific order of mixing. Thus components can be mixed in any order. Where there are three components then two components can be combined with each other, and then the combination may be combined with the third component, etc.

The term "pore size" in the context of a filter typically means the size of pores in the filter. Typically, the pore size is smaller or less than the size of the smallest viruses that can be removed by the filter. In this context, while certain embodiments of the invention may refer to geometric properties of pore size (e.g. diameter), it will be appreciated that pore size can be functionally defined, as will be described in more detail hereinafter.

It has surprisingly been found that when using guanidine hydrochloride (GuHCl) (sometimes also referred to as guanidine chloride or abbreviated as GdHCl, GdmCl or GndCl) according to the present invention, an Apo A-I solution can be filtered through a filter having pores with a pore size in the 15 nm to 35 nm range to achieve substantial or complete viral clearance, yet without aggregation of the proteins and clogging the filters. In particular embodiments the filter has a pore size in a range from 15 nm to 35 nm; or from 15 nm to less than 35 nm; or from 15 nm to 30 nm; or from 15 nm to 25 nm; or from 15 nm to 20 nm; or from 20 nm to 25 nm; or from 18 nm to 23 nm; or from 15 nm to 26 nm; or from 18 nm to 26 nm; or from 27 nm to 32 nm; or from 25 nm to 30 nm; or from 20 nm to 30 nm.

In embodiments of the invention, a filter having a pore size in a range from 15 nm to 35 nm has a mean pore size in the range from 15 nm to 35 nm. In some embodiments the filter has a mean pore size in the range from 15 nm to less than 35 nm; or from 15 nm to 30 nm; or from 15 nm to 26 nm; or from 18 nm to 26 nm; or from 15 nm to 25 nm; or from 15 to 20 nm; or from 20 nm to 25 nm; or from 18 nm to 23 nm; or from 27 nm to 32 nm; or from 25 nm to 30 nm; or from 20 nm to 30 nm. In particular embodiments the mean pore size is about 15 nm; or about 20 nm; or about 25 nm; or about 30 nm; or about 35 nm.

The use of GuHCl is beneficial from two points of view: 1) due to its chaotropic properties, GuHCl functions as an anti-aggregation agent and thus inhibits the formation of aggregate clusters of for example the Apo A-I proteins in solution; 2) however, it does not irreversibly affect the apolipoprotein structure so that once the GuHCl is removed, Apo A-I helices reform and the protein is able to associate with lipids to form particles, like reconstituted HDL. Moreover the apolipoprotein maintains its biological activity, which is highly important for the further use of the product as a pharmaceutical substance.

An advantage of the present invention is that it is possible to increase the rate of flow and to decrease the liquid volumes as well as the filter areas and process time needed for the filtration. As a result, larger amounts of the Apo A-I solution can be filtered within a short time, increasing the efficiency of the process substantially.

Viruses that can be removed efficiently with the present invention can have a size smaller than about 300 nm. The size of the viruses that can be removed suitably is smaller than about 200 nm. Examples of such viruses include cytomegalovirus (about 180-200 nm, plasma products); herpes simplex virus (about 150-200 nm, recombinant products); and epstein-barr virus (about 120-200 nm, recombinant antibody products). The size of the viruses that can be removed is preferably smaller than about 120 nm. Examples of such viruses include HIV (about 80-120 nm, plasma derived products). Normally, the viruses that can be removed are larger than about 20 nm, i.e. the approximate size of the parvo virus (15-26 nm, plasma and recombinant derived products). The parvo viruses, like B19 (plasma products) at about 18-26 nm in size are difficult to remove from a therapeutic protein source, so nanofiltration is typically considered a critical manufacturing step to evaluate for viral clearance as the filter pore sizes in the 20 nm range are close to the known size of the parvoviruses. Nevertheless, the process of the present invention allows for safe and efficient removal of small viruses such as members of the parvovirus family and hepatitis A (about 27-32 nm, plasma products), hepatitis B (about 42 nm, plasma products), hepatitis C (about 30-60 nm, plasma products) and encephalomyocarditis (about 25-30 nm; recombinant products) viruses. This is particularly noteworthy, since according to the state of the art, excessive amounts liquids for dilution are required in order to prevent aggregation of the proteins and clogging of the filters, which often resulted in break-through of small viruses.

In particular embodiments of the invention the filter has a pore size capable of removing from a solution comprising Apo A-I and guanidine hydrochloride (GuHCl) a parvovirus such as MVM or B19; and/or a hepatitis A virus; and/or a picomaviridae virus such as encephalomyocarditis virus.

Virus retention is suitably characterized in terms of the Log Reduction Value (LRV), which is defined as the logarithm (base 10) of the ratio of the viral concentration in the feed to that in the filtrate: LRV=−log 10S; where S is the sieving coefficient for the virus. The total required LRV depends on the nature and potential for viral contamination of the starting material. Virus filtration steps are typically designed to provide a minimum of 4-log virus removal (LRV). Viral clearance studies are performed by spiking high titer infectious viruses (with different physical characteristics) into scaled-down modules and evaluating the LRV. Removal of both enveloped and non-enveloped viruses may be demonstrated. Common model viruses include animal parvoviruses (e.g., MVM, B19), poliovirus (non-specific model virus), encephalomyocarditis virus (EMCV) (model for picomaviridae viruses like hepatitis A), simian virus 40 (SV40, non-specific model virus), sindbis virus (model for hepatitis C), bovine viral diarrhoea virus (BVDV, model for flaviviridae viruses like hepatitis C), duck hepatitis B virus (model for hepatitis B), Japanese Encephalitis virus (model for hepatitis C) and reovirus (non-specific model virus). Initial design studies can also be performed with bacteriophages which can be obtained at much higher purity and titers, and which are much easier (and less expensive) to assay.

Virus filtration validation studies are usually performed at small scale typically using self-contained devices with 13-47 mm discs. All process parameters are scaled down in a linear fashion and should represent worst-case conditions with regard to virus clearance. It is also important to process a larger amount of the feed stream per surface area compared with the industrial scale process design to insure validation under worst case process conditions. Virus clearance should be measured in several fractions. Several recent studies have demonstrated that virus clearance can decrease with the extent of membrane fouling (reduction in permeability) when using parvo-type virus filters (20 nm pore size).

The method of the present invention provides a very efficient way for inactivating and/or removing viruses. In principle, supposing that such high viral content is actually present, the present invention allows for the reduction of the content of very small non-enveloped viruses, such as the parvovirus by at least 3 log LRV (lowering the number of viruses by 1,000-fold), suitably by at least 4 log LRV (10,000-fold reduction), suitably by at least 5 log LRV (100,000-fold reduction) and preferably by at least 6 log LRV (1,000,000-fold reduction in the number of viruses).

In addition, the filtration method according to the invention can be easily combined with other virus removing or inactivating procedures, such as a heat treatment step, for ensuring even higher viral depletion.

Optionally, a pre-filtration or clarifying filtration step can be performed before the virus filtration in order to remove macro-size particles. Such a pre-filtration can also be performed with a filter comprising a membrane with a larger pore diameter than that of the virus-removing membrane. In an embodiment of the invention the pre-filter has a pore size in the range of 0.05-0.5 μm. In particular embodiments the pre-filters are selected from Pall Nylon membrane filter (SKL 7002 NTP 0.1 μm or FTKNI) or the Sartopore 2 filter. In particular embodiments the pre-filter size is chosen by using at least 0.025 m² of filter surface area per kg of starting material Apo A-I precipitate. In other embodiments the pre-filter size is chosen by using at least 0.014 m² of filter surface area per kg of starting material Apo A-I precipitate. In particular embodiments the pre-filter size is in the range from about 0.014 m² to about 0.035 m² of filter surface area per kg of starting material Apo A-I precipitate. The pre-filtration can be conducted either in line with the virus filter or out of line with respect to the virus filter. In particular embodiments the pre-filtration is conducted in line with respect to the virus filter. In particular embodiments the pre-filter is made from the same membrane material as the virus removing filter.

Suitable filters for the virus filtration method according to the invention are available commercially and can be purchased, for example, under the designations such as Planova BioEx (Asahi Kasei Corporation), inter alia. Such filters are sometimes referred to as 'small virus' removal filters.

In particular embodiments the virus removing filter comprises a membrane manufactured of one or more materials selected from cuprammonium regenerated cellulose, hydrophilic polyvinylidene fluoride (PVDF), composite PVDF, surface modified PVDF, nylon, and polyether sulfone.

In embodiments of the invention the filter membrane is a flat sheet or a hollow fibre membrane. Examples of flat sheet membranes include hydrophilised PVDF filter membranes such as the Pegasus™ Grade SV4 small-virus removal filters (Pall Corporation). In an embodiment the filter comprises a PVDF flat sheet membrane. In an embodiment the filter comprises a hydrophilic PVDF flat sheet membrane, or a composite PVDF flat sheet membrane, or a surface modified PVDF flat sheet membrane. In a particular embodiment the filter is the Pegasus™ Grade SV4.

In other embodiments the filter is a hollow fibre membrane. The hollow fibre membrane format typically contains a bundle of straw-shaped hollow fibres with the wall of each hollow fibre containing a 3 dimensional web structure of pores comprised of voids interconnected by fine capillaries. Examples of hollow fibre filters include the Planova™ BioEX filters (Asahi Kasei Corporation) which incorporates hydrophilic modified polyvinylidene fluoride (PVDF) in hollow fibre membrane format. In an embodiment the filter comprises a PVDF membrane in a hollow fibre membrane format. In an embodiment the filter comprises a hydrophilic PVDF hollow fibre membrane format, or a composite PVDF hollow fibre membrane format, or a surface modified PVDF hollow fibre membrane format. In particular embodiments the filter is the Planova™ BioEX.

For the purpose of comparing filter membranes that can have quite different structures it is not adequate to examine pore size using visual methods like microscopy. Hence reference to pore size, as described herein, describes a structural property of the filter assessed with functional methods, rather than visual methods. Estimation of the filter pore size can be made using a functional method. Such methods include bubble point measurements, liquid-liquid porosity, intrusion porosimetry, sieving of macromolecules (e.g. bacteriophages) and/or particles of defined sizes.

Mean flow bubble point can be measured according to ASTM E1294-89 ('Standard Test Method for Pore Size Characteristics of Membrane Filters Using Automated Liquid Porosimeter'). Briefly the method involves wetting the filter with perfluorohexane (e.g. Fluorinert™ FC-72) and then applying a differential pressure of air to remove the fluid. The differential pressure at which wet flow is equal to one half the dry flow (flow without wetting solvent) is used to calculate the mean flow pore size.

In particular embodiments of the invention the filter has a mean flow bubble point measured with perfluorohexane above 100 psi, or above 120 psi.

In other embodiments of the invention the pore size of the filter can be estimated by applying a colloidal gold particle solution to the filter (e.g. AGPTS—Asahi Kasei Corporation, gold particle test system). Prior to the beginning of the test, an in-line visual wavelength spectrometer measures the initial absorbance. As the gold particle solution passes through the filter, a second absorbance reading evaluates the gold particle removal rate and a pore size distribution result is determined based on an LRV calculation of the absorbance values.

The apolipoprotein may be any apolipoprotein which is a functional, biologically active component of a naturally-occurring HDL or of a reconstituted high density lipoprotein (rHDL). Particular apolipoproteins include members of the A, C and E families. Typically, the apolipoprotein is either a plasma-derived or recombinant apolipoprotein such as Apo A-I, Apo A-II, Apo A-V, pro-Apo A-I or a variant such as Apo A-I Milano or so called oxidation resistant forms such as 4WF. In particular embodiments the apolipoprotein is Apo A-I. In some embodiments the Apo A-I is derived from plasma. In other embodiments the Apo A-I is recombinant Apo A-I. Preferably, the Apo A-I is either recombinantly derived comprising a wild type sequence or the Milano sequence or it is purified from human plasma. The Apo A-I can be in the form of monomers, dimers, or trimers, or multimers or mixtures thereof. The apolipoprotein may be in the form of a biologically-active fragment of apolipoprotein. Such fragments may be naturally-occurring, chemically synthesized or recombinant. By way of example only, a biologically-active fragment of Apo A-I preferably has at least 50%, 60%, 70%, 80%, 90% or 95% to 100% or even greater than 100% of the lecithin-cholesterol acyltransferase (LCAT) stimulatory activity of Apo A-I.

The starting material containing an apolipoprotein like Apo A-I may be derived, for instance, from Precipitate IV according to Kistler and Nitschmann fractionation method, which has been further purified, e.g. by cold ethanol precipitation. In alternative embodiments the starting material containing an apolipoprotein like Apo A-I is a cell culture/fermentation extract. In embodiments the Apo A-I is produced by cell culture in a *E. coli* host/vector system or a mammalian host cell including but not limited to Chinese hamster ovary (e.g., CHO-KI or CHO-S), VERO, BHK, BHK 570, HeLa, COS-I, COS-7, MDCK, 293, 3T3, PC12 and W138, or from an amyeloma cell or cell line (e.g., a murine myeloma cell or cell line). In particular embodiments the cell cultures may be cultivated in a serum free medium. In embodiments the cell cultures may be cultivated in a serum free medium lacking animal derived components.

Before use, Apo A-I precipitate may be stored at a temperature below −20° C. in the freezer.

For suspending the Apo A-I precipitate, the volume ratio of Apo A-I precipitate to solution can be in the range from 1:2 to 1:5. In some embodiments the volume ratio of Apo A-I precipitate to solution is in the range 1:3 to 1:4. In particular embodiments the volume ratio of Apo A-I precipitate to solution is 1:3, or 1:3.1, or 1:3.2, or 1:3.3, or 1:3.4, or 1:3.5.

In order to facilitate the re-suspension, the frozen Apo A-I precipitate can be broken into small pieces (<5 cm of diameter) inside a polyethylene bag by using e.g. a pharma-hammer before adding the frozen Apo A-I precipitate to the solution.

The suspension can be subsequently diluted with WFI (water for injection) for adjusting the Apo A-I protein concentration and the GuHCl concentration in the solution to the desired range.

In some embodiments the solution comprising Apo A-I and guanidine hydrochloride (GuHCl) is derived from a purified Apo A-I as described in PCT/AU2014/000584.

In the context of the present invention, the expression "5 to 30 g/L Apo A-I" and similar expressions mean that 5 to 30 g of apolipoprotein A-I (Apo A-I) protein is solubilized in 1 L solution. The apolipoprotein concentration for the filtration step is typically in the range of 0.5 g/L to 50 g/L. In particular embodiments the Apo A-I protein concentration in the solution of step a) is in the range from 5 to 25 g/L; or 5 to 20 g/L; or 5 to 15 g/L; or 5 to 12 g/L; or 7 to 12 g/L; or 5 to 11 g/L; or 7 to 11 g/L; or 5 to 10 g/L; or 7 to 10 g/L. In some embodiments of the invention the protein concentration of the solution comprising Apo A-I and guanidine hydrochloride (GuHCl) is determined by measuring the absorbance at 280 nm and then calculating the protein concentration as described in Example 1. In some embodiments the protein concentration of the solution comprising Apo A-I and guanidine hydrochloride (GuHCl) is determined by nephelometry or high performance capillary electrophoresis (using the method described in Example 1).

It is particularly preferred that the GuHCl concentration of the solution of step a) is within the range from 1.3 to 3.2 M. In particular embodiments the GuHCl concentration is within the range from 1.3 to 3.0 M; or 1.3 to 2.75 M; or 1.3 to 2.5M; or 1.5 to 3.0 M; or 1.5 to 2.75 M; or 1.5 to 2.5 M; or 1.5 to 2.25 M; or 1.5 to 2.0 M; or 1.5 to 1.9 M. More preferably the GuHCl concentration is within the range from 1.6 to 1.9 M and most preferably the GuHCl concentration is 1.7 M. This concentration is ideal to suppress aggregate formation of the Apo A-I protein in the solution, improve the filterability (i.e. capacity and throughput) and ensure maximum retention of virus in the filter membrane (i.e. selectivity). In embodiments of the invention the concentration of GuHCl of the solution comprising Apo A-I and guanidine hydrochloride (GuHCl) is determined using ion exchange chromatography. In particular embodiments of the invention the guanidine content is determined using ion chromatography (HPLC) with a suitable cation exchange column (e.g. IonPac CS19 analytical column, 4×250 mm (Thermo Scientific, Dionex)). The Dionex IonPac CS19 column can be used with a Reagent-Free™ Ion Chromatography (RFIC™) system for automatic methanesulfonic acid (MSA) eluent generation and electrolytic eluent suppression with conductivity detection. In this way the background due to ions from the mobile phase (e.g. methane sulfonic acid, MSA) are suppressed and detection of the guanidine can be carried out by measuring the conductivity. Samples containing the Apo A-I and guanidine can be mixed with an internal standard (e.g. formamidine acetate) and diluted in water so that the guanidine concentration is about 0.1-2.0 mg/mL. The chromatography can be run in either isocratic or gradient modes. The quantification can be based on the peak area with a five point calibration (0.1-2.0 mg/mL) and the internal standard.

According to an embodiment, the pH of the solution before the virus filtration step is within the range from about 7 to about 10; or from about 7 to about 9; or from about 7 to about 8. In particular embodiments the pH of the solution before the virus filtration step is within the range from 7.1 to 7.5. In a further embodiment the pH of the solution before the virus filtration step is at 7.3. This pH range is at physiological (about 7.35-7.45) or nearly at physiological pH. Ideally the pH will be at least one pH unit away from the isoelectric point of the apolipoprotein. In particular embodiments the pH is at least one pH unit away from the isoelectric point of the apolipoprotein. In the case of human Apo A-I and variants thereof the isoelectric point is typically in the range of about pH 5.2 to 5.8. The isoelectric point of an apolipoprotein can be determined by isoelectric focusing (IEF) such as by the method described in Contiero et. al. (1997) Electrophoresis 18(1), 122-126. When multiple apolipoprotein isoform peaks are present in the IEF profile then the mean isoelectric point can be used.

In the context of the present invention, when the pH of a solution is within a given 10 pH range, e.g. a range from 7.1 to 7.5, this means that the solution "has" a pH of that range, e.g. a pH of 7.1 to 7.5. This means that the solution is formed at a pH of 7.1 to 7.5, or is after its formation brought to a pH of 7.1 to 7.5.

In general, the pH is measured either in the solution before adding the Apo A-I protein to said solution; or directly after mixing the Apo A-I protein with the solution. Typically, the pH of the solution of step a) is measured right after mixing the precursor components. Alternatively, the pH of the mixture can also be determined by calculation based on the projected amounts and concentrations of the components in the mixture.

In the present invention, solution refers to a solution that contains at least 50 percent by weight of water, optionally including one or more solvents, such as methanol or ethanol. The solvents can be any pharmaceutical grade solvent. In particular embodiments of the invention the solvent is ethanol for example 95% pharmaceutical grade ethanol (e.g. 3 A containing 5% methanol). In a further embodiment the solution comprises about 20% ethanol.

Optionally the filter used in step a) is prewashed with WFI and/or GuHCl solution before filtering the solution. This prewashing step increases the permeability of the proteins through the filter. In a particular embodiment the filter is prewashed with 1.3 to 2.0 M GuHCl.

In order to minimize the loss of protein through the virus filtration, in some embodiments after the filtration, the filter is post-washed with GuHCl. In particular embodiments the filter is post-washed with 1.3 to 2.0 M GuHCl.

The virus filtration can be performed using either tangential flow filtration (TFF) or 'dead-end' filtration (also known as normal or direct flow filtration). Virus filters were originally designed for use in TFF with the feed flowing adjacent to the upper skin layer of the asymmetric membrane. TFF provides high flux by sweeping the membrane surface to reduce concentration polarization and fouling. However, the simplicity and lower capital cost of dead end filtration has led to the widespread use of virus filters specifically designed for dead end filtration. In contrast to TFF, these dead end filters are typically operated with the more open side of the membrane facing the feed stream, allowing protein aggregates and other large foulants to be captured within the macroporous substructure thereby protecting the virus-retentive skin layer. Advantages of using single-use dead end filters include that they simplify both system design and validation, reducing labor and capital costs.

Dead-end filtering typically involves using a single pump to force fluid through the membrane from the surface.

Tangential filtration generally requires a first pump to maintain constant flow rate at the surface of the filter membrane and a second pump draws the protein through the membrane by creating a negative pressure at the back of the membrane.

In particular embodiments the filtration is performed by dead-end filtration.

In particular embodiments the dead-end filtration process is conducted using either constant pressure filtration or constant velocity filtration. In a particular embodiment the dead-end filtration process is conducted using constant pressure filtration.

Filtration is performed with filtration pressure that is the same as or below the level at which the membrane can withstand, depending on the material of a virus-removing membrane to be used herein, for example with pressures of about 0.2 to about 3.4 bar. In particular embodiments the filtration pressure is maintained between about 0.2 bar to about 3.4 bar. In embodiments the filtration pressure is maintained at about 1 to about 3 bar; or at about 1.5 to about 3 bar, or at about 1.7 to about 3 bar; or at about 2 to about 3 bar; or at about 2.2 to about 3 bar; or at about 2.2 to about 2.7 bar. In embodiments the filtration pressure is maintained at about 1.7 bar to about 2.4 bar; or at about 2.2 bar to about 2.4 bar.

The temperature has an effect on the viscosity of a protein solution and also has an effect on the flux upon filtration with a virus-removing membrane. The solution to be used in the filtration step should have a temperature within the range from 0° C. up to the temperature at which the protein concerned is denatured. The temperature of the solution suitably is within the range of from about 10° C. up to about 50° C. In particular embodiments the temperature of the solution is within the range of from about 18° C. up to about 35° C. In some embodiments the solution is filtered at room temperature from about 18° C. to about 26° C.

In particular embodiments two or more filters are used in series. In a particular embodiment the filtration is conducted using two filters in series having a pore size in a range from 15 nm to 35 nm. In some embodiments the two or more filters have a pore size in the range from 15 nm to less than 35 nm; or from 15 nm to 30 nm; or from 15 nm to 25 nm; or from 15 to 20 nm; or from 20 nm to 25 nm. In particular embodiments the two or more filters have a mean pore size selected from the group of about 15 nm; or about 20 nm; or about 25 nm; or about 30 nm; or about 35 nm.

In embodiments of the invention the virus filter capacity is at least 200 kg or at least 300 kg or at least 340 kg or at least 500 kg or at least 750 kg or at least 1000 kg of the solution comprising Apo A-I and GuHCl per $m^2$ of filter surface area.

The solution of step a) can be prepared by suspending Apo A-I precipitate in a solution comprising 4.0 to 4.6 M GuHCl and subsequently diluting the suspension to a desired Apo A-I protein concentration within the range from 5 to 30 g/L and to a desired GuHCl concentration within the range from 1.3 to 3.2 M.

In particular embodiments of the invention the method for purifying apolipoprotein (Apo A-I) comprises filtering a solution comprising 5 to 30 g/L Apo A-I at a pH from about 7 to about 8 and guanidine hydrochloride (GuHCl) at a concentration of 1.3 to 3.2 M. Wherein, the filter has a pore size in a range from 15 nm to 35 nm and the filtration is a dead-end filtration at a pressure of about 1 to about 3 bar and a temperature of about 18° C. to about 35° C.

In particular embodiments of the invention the method for purifying apolipoprotein (Apo A-I) comprises filtering a solution comprising 5 to 20 g/L Apo A-I at a pH from about 7 to about 8 and guanidine hydrochloride (GuHCl) at a concentration of 1.5 to 3.0 M. Wherein, the filter has a pore size in a range from 15 nm to less than 35 nm and the filtration is a dead-end filtration at a pressure of about 1 to about 3 bar and a temperature of about 18° C. to about 35° C.

In particular embodiments of the invention the method for purifying apolipoprotein (Apo A-I) comprises filtering a solution comprising 5 to 20 g/L Apo A-I at a pH from about 7 to about 8 and guanidine hydrochloride (GuHCl) at a concentration of 1.5 to 2.0 M. Wherein, the filter has a pore size in a range from 15 nm to 26 nm and the filtration is a dead-end filtration at a pressure of about 1 to about 3 bar and a temperature of about 18° C. to about 35° C.

As a routine practice, virus filters are integrity tested pre- and post-use to ensure that the filter achieves the required level of performance. To facilitate this, filter manufacturers have developed a variety of destructive and non-destructive physical integrity tests. The purposes of these physical integrity tests are to confirm that (1) the virus filter is properly installed; (2) the filter is free from defects and damages; and (3) the performance of the filters is consistent with both manufacturers' specifications and end-user virus retention studies. The most commonly used nondestructive tests include the bubble point test, the forward flow test (e.g. Palltronic Flowstar XC (Pall)), the water intrusion test and the binary gas test. Both the bubble point test and the forward flow test evaluate a wet membrane as a barrier to the free flow of a gas. The water intrusion test, also called HydroCorr test, uses a dry hydrophobic membrane as a barrier to the free flow of water, a non-wetting fluid. The binary gas test uses a mixture of two gases with high differences in permeability, and the test is based on measurement of the composition of the gas mixture upstream and downstream of a water-wetted membrane. The gold particle test, the post-use integrity test used with Planova (Asahi Kasei Corporation) filters, is a destructive integrity test. Generally, nondestructive tests are used due to the option of retesting filter integrity if the initial test fails. If the post-use integrity tests and retests fail, re-filtration is a common practice for virus filtration steps. These tests can additionally be used to estimate filter pore size, as described above.

According to a particular embodiment of the present invention, the method further comprises a heat treatment step for further viral depletion. In a preferred embodiment said heat treatment step is conducted prior to step a) (Option I). In an alternative embodiment said heat treatment step is conducted after step b) (Option II).

The apolipoprotein concentration for the heat inactivation step is typically in the range of 0.5 to 50 g/L. In particular embodiments that Apo A-I protein concentration is within the range from 5 to 30 g/L.

According to Option I of the above embodiment, the heat treatment step is performed prior to step a), thus before the virus filtration. In this case, a solution comprising GuHCl, e.g. in a concentration of 2.7 to 3.9 M, and Apo A-I at a pH of 6.6 to 10.0, in particular embodiment at a pH of 6.6 to 8.0, is provided in a first step. The solution is then subsequently heated at temperature of 55 to 61° C. for about 30 minutes to about 4 hours in order to inactivate viruses that may still be present in the solution.

According to Option II of the above embodiment, the heat treatment step is conducted after step b), thus after the virus filtration. In this case, the GuHCl concentration in the solution after step b) is adjusted to provide a solution comprising GuHCl, e.g. in a concentration of 2.7 to 3.9 M, and at a pH of 6.6 to 8.0. The solution is then subsequently heated at temperature of 55 to 61° C. for about 30 minutes to about 4 hours in order to inactivate viruses, which may still be present in the solution.

For both options, Option I and Option II, the GuHCl concentration of the solution with a pH of 6.6 to 8.0 preferably is within the range from 3.0 to 3.9 M and is most preferably 3.5 M. Within this concentration range, aggregate formation of the proteins in the solution is suppressed.

In an embodiment the pH of the solution with a pH of 6.6 to 8.0 is within the range from 7.0 to 8.0. In particular embodiments the pH of the solution is at or about 7.3. This means that the method according to the present invention is performed at physiological (about 7.35-7.45) or nearly physiological pH, which reduces the risk of the target proteins denaturizing and losing their biological activity.

In the case of Option I, where the heat treatment step is performed prior to the virus filtration, the solution with a pH of 6.6 to 8.0 is preferably prepared by suspending Apo A-I precipitate in a 4.0 to 4.6 M GuHCl and then subsequently adjusting the GuHCl concentration within the range from 2.7 to 3.9 M and the pH within the range from 6.6 to 8.0, e.g. by dilution. The GuHCl concentration may in particular be within the range from 2.7 to 3.5 M.

After the heat treatment, the solution for step (a) is prepared from the solution with a pH within the range from 6.6 to 8.0 by adjusting the Apo A-I protein concentration and the GuHCl concentration to the desired range of the solution (A), e.g. by diluting the solution with WFI.

In the case of Option II, where the heat treatment step is performed after the virus filtration, the solution with a pH of 6.6 to 8.0 is preferably prepared from the solution after step b) by adjusting the Apo A-I protein concentration of the solution within the range from 5 to 30 g/L and the GuHCl concentration of the solution within the range from 1.3 to 3.2 M.

The specific combination of the solution comprising GuHCl and having a pH within the range from 6.6 to 8.0, makes viral clearance much faster than according to the previously known pasteurization procedures, namely within about 30 minutes to about 4 hours at 60° C. instead of the well-established 10 hours methods.

Due to the reduced time needed for achieving viral clearance, the method of the present invention is particularly well suited for use in industrial applications, where time is a key factor.

Furthermore, due to the shortened time that the target protein is exposed to elevated temperatures, the risk that the protein is irreversibly denatured is greatly lowered even without the addition of stabilizers and therefore without risking the impairment of protein function. This makes the method of the present invention particularly suitable for viral removal from protein intended for therapeutic use or as a vehicle for therapeutic delivery.

Whilst the above heat treatment method is preferred it is recognised that the heat treatment step can also involve more traditional methods, like heating the Apo A-I solution at 60° C. for at least 10 hours.

The combination of the heat treatment and filtration steps has the potential to enable Apo A-I to be manufactured with at least LRV 12 log LRV for parvoviruses like MVM, at least LRV 9 log for non-enveloped viruses like EMCV, and at least LRV 8.5 log for lipid enveloped viruses like BVDV.

The present invention provides an Apo A-I preparation with at least 12 log LRV (log reduction value) for a parvovirus; and/or at least 9 log LRV for a non-enveloped virus; and/or at least 8.5 log LRV for a lipid enveloped virus. In some embodiments of the present invention provides an Apo A-I preparation with at least 12 log LRV (log reduction value) for a parvovirus; and/or at least 9 log LRV for a non-enveloped virus. In some embodiments of the present invention provides an Apo A-I preparation with at least 12 log LRV (log reduction value) for a parvovirus. In particular embodiments the parvovirus is MVM. In particular embodiments the non-enveloped virus is a picornaviridae virus, such as EMCV. In particular embodiments the lipid enveloped virus is a flaviviridae virus. In particular embodiments the Apo A-I preparation is suitable for pharmaceutical use. In particular embodiments of the invention the MVM and/or EMCV LRV for the Apo A-I preparation is determined by the method of Example 6.

The solutions used in the invention may further comprise additives, for example EDTA. In particular embodiments EDTA is added in a concentration of about 1 mM.

Whilst the methods of the present invention can be performed at laboratory scale, they can be scalable up to industrial size without significant changes to conditions. Thus, in an embodiment disclosed herein, the methods of the present invention are performed on an industrial or commercial scale. Preferably, the methods of the invention are suitable for the commercial scale manufacture of human apolipoprotein A-1 (Apo A-I). For example, when using plasma fractions as a starting material in the method of the invention, then commercial scale manufacture would involve the use of a plasma fraction derived from at least about 500 kg of plasma. More preferably, the starting plasma fraction will be derived from at least about 5,000 kg, 7,500 kg, 10,000 kg and/or 15,000 kg of plasma per batch.

The purified apolipoprotein may subsequently be formulated with other components to make a pharmaceutical composition, e.g. to make reconstituted HDL (rHDL). The methods of the invention may therefore comprise an additional step of mixing the purified apolipoprotein with a lipid to make an rHDL formulation. As used herein, an rHDL formulation may be any artificially-produced apolipoprotein formulation or composition that is functionally similar to, analogous to, corresponds to, or mimics, high density lipoprotein (HDL) typically present in blood plasma. rHDL formulations include within their scope "HDL mimetics" and "synthetic HDL particles". Suitably, the rHDL formulation comprises an apolipoprotein, a lipid and, optionally, a detergent.

rHDL formulations of the invention may further comprise cholesterol. The formulations may be produced using organic solvents, which in some cases are used for dissolving the lipid component (e.g. phosphatidylcholine) when producing the formulation, such as described in U.S. Pat. No. 5,652,339. However it is preferred that the apolipoprotein formulation is produced in the absence of organic solvent.

Suitably, the apolipoprotein is at a concentration of about 5-100 g/L, preferably 10-50 g/L or more preferably 25-45 g/L. This includes 5, 10, 15, 20, 25, 30, 35, 40, 45, 50, 55, 60, 65, 70, 75, 80, 85, 90, 95 and 100 g/L and any ranges between these amounts. In other embodiments, the apolipoprotein may be at a concentration of from about 5 to 20 g/L, e.g. about 8 to 12 g/L.

The lipid may be any lipid which is a component of naturally-occurring HDL or of reconstituted high density lipoprotein (rHDL). Such lipids include phospholipids, cholesterol, cholesterol-esters, fatty acids and/or triglycerides. Preferably, the lipid is a phospholipid. Non-limiting examples of phospholipids include phosphatidylcholine (PC) (lecithin), phosphatidic acid, phosphatidylethanolamine (PE) (cephalin), phosphatidylglycerol (PG), phosphatidylserine (PS), phosphatidylinositol (PI) and sphingomyelin (SM), sphingosine-1 phosphate or natural or synthetic derivatives thereof. Natural derivatives include egg PC, egg PG, soy bean PC, hydrogenated soy bean PC, soy bean PG, brain PS, sphingolipids, brain SM, galactocerebroside, gangliosides, cerebrosides, cephalin, cardiolipin, and dicetylphosphate. Synthetic derivatives include dipalmitoylphosphatidylcholine (DPPC), didecanoylphosphatidylcholine (DDPC), dierucoylphosphatidylcholine (DEPC), dimyristoylphosphatidylcholine (DMPC), distearoylphosphatidylcholine (DSPC), dilaurylphosphatidylcholine (DLPC), palmitoyloleoylphosphatidylcholine (POPC), palmitoylmyristoylphosphatidylcholine (PMPC), palmitoylstearoylphosphatidylcholine (PSPC), dioleoylphosphatidylcholine (DOPC), dioleoylphosphatidylethanolamine (DOPE), dilauroylphosphatidylglycerol (DLPG), distearoylphosphatidylglycerol (DSPG), dimyristoylphosphatidylglycerol (DMPG), dipalmitoylphosphatidylglycerol (DPPG), distearoytphosphatidylglycerol (DSPG), dioleoylphosphatidylglycerol (DOPG), palmitoyloleoylphosphatidylglycerol (POPG), dimyristoylphosphatidic acid (DMPA), dipalmitoylphosphatidic acid (DPP A), distearoylphosphatidic acid (DSPA), dimyristoylphosphatidylethanolamine (DMPE), dipalmitoylphosphatidylethanolamine (DPPE), dimyristoylphosphatidylserine (DMPS), dipalmitoylphosphatidylserine (DPPS), distearoylphosphatidylethanolamine (DSPE), dioleoylphosphatidylethanolamine (DOPE) dioleoylphosphatidylserine (DOPS), dipalmitoylsphingomyelm (DPSM) and distearoylsphingomyelin (DSSM). The phospholipid can also be a derivative or analogue of any of the above phospholipids.

In some embodiments the lipid component of the rHDL comprises at least two different phosphatidylcholines. In particular embodiments the at least two phosphatidylcholines is a palmitoyl-oleoyl-phosphatidylcholine (POPC) and a di-palmitoy-Iphosphatidylcholine (DPPC). In particular embodiments the reconstituted HDL formulation of the present invention comprises POPC and DPPC. In particular embodiments the ratio of the POPC:DPPC is about 75:25; or about 50:50.

In other specific embodiments, the lipid is, or comprises, sphingomyelin in combination with a negatively charged phospholipid, such as phosphatidylglycerol (e.g. 1,2-dipalmitoyl-sn-glycero-3-[phospho-rac-(I-glycerol)). A combination of sphingomyelin and phosphatidylglycerol (particularly 1,2-dipalmitoyl-sn-glycero-3-[phospho-rac-(I-glycerol)) is specifically envisaged for use as the lipid. In these embodiments, the sphingomyelin and the phosphatidylglycerol may be present in any suitable ratio, e.g. from 90:10 to 99:1 (w:w), typically 95:5 to 98:2 and most typically 97:3.

Preferably the phospholipid is, or comprises, phosphatidylcholine, alone or in combination with one or more other phospholipids. An example of another phospholipid is sphingomyelin. In some embodiments, the apolipoprotein formulation may comprise a detergent.

Typically, although not exclusively the lipid may be present at a concentration of 10-100 g/L or preferably 30-60 g/L.

The detergent may be any ionic (e.g. cationic, anionic, Zwitterionic) detergent or non-ionic detergent, inclusive of bile acids and salts thereof, suitable for use in rHDL formulations. Ionic detergents may include bile acids and salts thereof, polysorbates (e.g. PS80), CHAPS, CHAPSO, cetyl trimethyl-ammonium bromide, lauroylsarcosine, n-octyl-N,N-dimethyl-3-ammonio-1-propane sulfonate, n-decyl-N,N-dimethyl-3-ammonio-1-propane sulfonate and 4'-amino-7-benzamido-taurocholic acid.

Bile acids are typically dihydroxylated or trihydroxylated steroids with 24 carbons, including cholic acid, deoxycholic acid chenodeoxycholic acid or ursodeoxycholic acid. Preferably, the detergent is a bile salt such as a cholate, deoxycholate, chenodeoxycholate or ursodeoxycholate salt. A particularly preferred detergent is sodium cholate.

However, high levels of detergent have been shown to be associated with liver toxicity in some systems, e.g. levels of 0.3 g/g Apo-AI or 6 g/L rHDL formulation (at 20 g/L Apo-AI). Accordingly, 5-10% of this level of detergent is preferred for use in the invention, i.e. 0.015-0.03 g/g Apo-AI or 0.5-0.9 g/L rHDL formulation (at 30 g/L Apo-AI). The "level" of detergent may be an absolute amount of detergent, a concentration of detergent (e.g. mass per unit volume of rHDL formulation) and/or a ratio of the amount or concentration of detergent relative to another amount or concentration of a component of the rHDL formulation. By way of example only, the level of detergent may be expressed in terms of the total mass of apolipoprotein (e.g. Apo-AI) present in the rHDL formulation. A detergent concentration no less than about 0.45 g/L of rHDL formulation with 30 g/L apolipoprotein is optimal in terms of both stability and non-toxicity. Stability may advantageously be measured by any means known in the art, although turbidity of the rHDL formulation is a preferred measure. In particular embodiments the detergent concentration is between 0.5-1.5 g/L in the rHDL formulation. The detergent concentration can be determined using a colorimetric assay. For example using the Gallsäuren test kit and Gallsäuren Stoppreagens with plasma added to the reaction vials (125 μL plasma in 1 mL reaction volume).

More generally, the level of detergent when present in the rHDL formulations of the invention is about 5-35% of that which displays liver toxicity. This range includes, for example, 5%, 10%, 15%, 20%, 25%, 30% and 35%. More preferably, the level of detergent is about 5-20% of that which displays liver toxicity. Advantageously, the level is about 5-10% of that which displays liver toxicity. Preferably, these levels are expressed in terms of the minimum or threshold level of detergent that displays liver toxicity. Liver toxicity can be evaluated by various in vitro and in vivo models. One example of an in vitro model uses HEP-G2 cells. This involves growing HEP-G2 cells into the log phase. The cells are then removed from the culture medium and washed in PBS prior to trypsinization and resuspension in 10 mL of culture medium (90% DMEM, 10% inactivated FCS, 1% nonessential amino acids, 1% Pen/Strep). Cell growth and viability are monitored using a Neubauer haemocytometer and trypan blue staining. Aliquots of 100 μL containing $10 \times 10^4$ C/mL are subsequently seeded, into 96 well F-bottom plates and incubated overnight at 37° C., 5% $CO_2$, 95% $H_2O$. Samples (700 μL) containing the test articles (e.g rHDL formulations) are prepared by addition of culture medium. The medium from the first row of wells is removed and 200 μL of the test article solution added. A serial 1:2 dilution series is completed on the plates. The plates are then incubated for 72 hours at 37° C., 5% $CO_2$, 95% $H_2O$. After which the cell viability is determined. This can be done by adding 50 μL of 3× Neutral Red Solution (70 mg Neutral Red in 100 mL PBS) to each well. The plates are incubated for 2 hours at 37° C., 5% $CO_2$, 95% $H_2O$ and the wells washed once with 200 μL PBS. After this, 100 μL of ethanol is added to each plate and the plates shaken for 20 minutes prior to being read at 540 nm. An example of an in vivo hepatoxicity model is the conscious rabbit model. The model uses rabbits which have been placed in a restraint device (rabbit holder) and i.v. catheters inserted into their ear veins. Test articles are given as a 40 minute i.v. infusion. Blood samples are taken from the ear artery and collected into serum and streptokinase-plasma (5%) vials. Blood samples are processed to serum, stored at −20° C. and to plasma and stored at −80° C. Samples can then be assessed for the level of ALT and AST activity using enzymatic photometric test kits available commercially (Greiner Biochemica). Whilst human Apo A-I levels can be determined using a nephelometric assay or high performance capillary electrophoresis.

In a further preferred embodiment, the rHDL formulation comprises a lipid at a level that does not cause liver toxicity. Suitably, the level of lipid is about 20-70% of that which causes, or is associated with, liver toxicity. In particular embodiments, the level of lipid is preferably about 25%, 30%, 35%, 40%, 45%, 50%, 55%, 60% or 65% of that which causes, or is associated with, liver toxicity, and any ranges between these amounts. Preferably, these levels are expressed in terms of the minimum or threshold level of lipid that displays liver toxicity. By way of example, a level of lipid which has been shown to be associated with liver toxicity is 84 g L. Accordingly the lipid is preferably at a concentration of about 30-60 g/L. This includes 30, 35, 40, 45, 50, 55 and 60 g/L and any ranges between these amounts. A particularly advantageous concentration of lipid is about 30-50 g/L, or in certain embodiments about 34 or 47 g/L. The "level" of lipid may be an absolute amount of lipid, a concentration of lipid (e.g. mass per unit volume of rHDL formulation) and/or a ratio of the amount or concentration of lipid relative to another amount or concentration of a component of the fixed dosage apolipoprotein formulation. By way of example only, the level of lipid may be expressed in terms of a molar ratio of apolipoprotein (e.g. Apo-AI) present in the fixed dosage rHDL formulation.

In one preferred embodiment, the molar ratio of apolipoprotein:lipid in the rHDL formulations of the invention is in the range 1:20 to 1:100. This range includes molar ratios such as 1:30, 1:40, 1:50, 1:60, 1:70, 1:80 and 1:90. More preferably, the molar ratio of apolipoprotein:lipid is in the range of 1:40 to 1:80; or 1:40 to 1:75; or 1:45 to 1:70; or 1:40 to 1:65; or 1:40 to 1:60; or 1:40 to 1:55; or 1:40 to 1:50; or 1:45 to 1:80; or 1:45 to 1:75; or 1:45 to 1:70; or 1:45 to 1:65; or 1:45 to 1:60; or 1:45 to 1:55; or 1:50 to 1:80; or 1:50 to 1:75; or 1:50 to 1:65; or 1:50 to 1:60. A particularly advantageous ratio of apolipoprotein:lipid is about 1:40; or about 1:45; or about 1:50; or about 1:55; or about 1:60.

In other embodiments, the molar ratio of apolipoprotein:lipid in the rHDL formulations of the invention is in the range from about 1:80 to about 1:120. For example, the ratio may be from 1:100 to 1:115, or from 1:105 to 1:110. In these embodiments, the molar ratio may be for example from 1:80 to 1:90, from 1:90 to 1:100, or from 1:100 to 1:110.

In a particular embodiment, the present invention provides an rHDL formulation obtained by the method of the invention.

In a particular embodiment, the invention provides an rHDL formulation comprising an Apo A-I preparation with at least 12 log LRV (log reduction value) for a parvovirus; and/or at least 9 log LRV for a non-enveloped virus; and/or at least 8.5 log LRV for a lipid enveloped virus. In some embodiments of the present invention provides an rHDL formulation comprising an Apo A-I preparation with at least 12 log LRV (log reduction value) for a parvovirus; and/or at least 9 log LRV for a non-enveloped virus. In some embodiments of the present invention provides an Apo A-I preparation with at least 12 log LRV (log reduction value) for a parvovirus. In particular embodiments the parvovirus is MVM. In particular embodiments the non-enveloped virus is a picomaviridae virus, like EMCV. In particular embodiments the lipid enveloped virus is a flaviviridae virus. In particular embodiments of the invention the MVM and/or EMCV LRV for the Apo A-I preparation comprised in the rHDL formulation is determined by the method of Example 6. In particular embodiments the rHDL formulation is suitable for pharmaceutical use.

The skilled person would understand that additional purification/fractionation steps to the two dedicated virus reduction steps of virus filtration and heat inactivation can potentially provide further levels of virus clearance for the Apo A-I preparations and rHDL formulations of the present invention. For example high ethanol concentrations which are often used when obtaining Apo A-I rich fractions from plasma have been shown to inactivate viruses (Hénin et. al., 1988, Vox Sang. 54(2):78-83). In such situations the LRV of these steps can be added to the overall LRV for the Apo A-I preparations or rHDL formulations of the present invention.

Purified Apo A-I as hereinbefore described can be formulated into pharmaceutical compositions, such as into reconstituted HDL for therapeutic use (including as described above). Such pharmaceutical compositions may include a pharmaceutically acceptable carrier or diluent. Non-limiting examples of pharmaceutically acceptable carriers or diluents include water, emulsifiers, binders, fillers, surfactants, buffers, stabilizers, salts, alcohols and polyols, detergents, proteins and peptides, lipids, gums, sugars and other carbohydrates, although without limitation thereto.

Reconstituted HDL may, in addition to Apo-AI, comprise one or more of a lipid, a detergent and a stabilizer, although without limitation thereto. Non-limiting examples of lipids include phospholipids, cholesterol, cholesterol-esters, fatty acids and/or triglycerides. Preferably, the lipid is a phospholipid. Non-limiting examples of phospholipids include phosphatidylcholine (PC) (lecithin), phosphatidic acid, phosphatidylethanolamine (PE) (cephalin), phosphatidylglycerol (PG), phosphatidylserine (PS), phosphatidylinositol (PI) and sphingomyelin (SM) or natural or synthetic derivatives thereof. Stabilizers may be a carbohydrate such as a sugar (e.g. sucrose) or a sugar alcohol (e.g. mannitol or sorbitol), although without limitation thereto. If present, the detergent may be any ionic (e.g cationic, anionic, Zwitterionic) detergent or non-ionic detergent, inclusive of bile acids and salts thereof, such as sodium cholate.

In particular embodiments the pharmaceutical compositions are described in WO2014/066943.

The invention also provides a method of treating or preventing a disease, disorder or condition in a mammal including the step of administering to the mammal Apo-A1, an Apo-A1 preparation, a pharmaceutical composition or an rHDL formulation according to any of the aforementioned aspects to a mammal to thereby treat or prevent the disease, disorder or condition.

Therapeutic uses for Apo A-1 and/or reconstituted HDL formulations may include treatment or prophylaxis of cardiovascular disease (e.g. acute coronary syndrome (ACS, atherosclerosis and myocardial infarction) or diseases, disorders or conditions such as diabetes, stroke or myocardial infarction that predispose to ACS, hypercholesterolaemia (e.g. elevated serum cholesterol or elevated LDL cholesterol) and hypocholesterolaemia resulting from reduced levels of high-density lipoprotein (HDL), such as is symptomatic of Tangier disease.

Certain embodiments of the invention will now be described with reference to the following examples which are intended for the purpose of illustration only and are not intended to limit the scope of the generality hereinbefore described.

EXAMPLES

Example 1

The following example describes a sequential arrangement of the process steps according to a preferred embodiment of the process according to the present invention. This process includes a Fraction IV precipitate derived starting material being dissolved in the presence of GuHCl, filtered to remove filter aids prior to pH adjustment, heat treatment, dilution and virus filtration. The heat treatment can alternatively also be performed after the virus filtration step.

Methods and Materials

Apo A-I Protein Concentration

Generally, the Apo A-I protein concentration in solution was measured by determining the absorbance at 280 nm using WFI (water of injection) as diluent and is typically 5 to 30 g/L. The protein calculation is as follows:

$$\text{Protein concentration [g/L]} = \frac{\text{Measured Absorbance} \times 0.885 \times \text{Dilution}}{1.0844}$$

Alternatively the Apo A-I protein concentration can be determined using either nephelometry or high performance capillary electrophoresis (Hewlett Packard 3D CE, Agilent Technology). Briefly, in relation to high performance capillary electrophoresis the method included the following steps—samples (150 μL) containing approximately 2-3 mg/mL Apo A-I (if necessary diluted with water) were prepared with 16% SDS (25 μL) and phenylalanine (25 μL, 4 mg/mL). The samples were then incubated in a water bath for 3 minutes prior to dilution in an electrophoresis buffer (50 mM sodium borate, 0.2% SDS, 300 μL) and filtered (0.45 μm). The samples were then loaded onto a fused silica capillary (56 cm by 50 μm id, Agilent G1600-61232). Electrophoresis was carried out at 25 kV. The standard used was an International Apo A-I Standard (BCR-393). This method is particularly useful when the Apo A-I is part of a reconstituted HDL.

4.6 M Guanidine Hydrochloride Solution

The 4.6 M GuHCl solution with 1 mM EDTA (Titriplex) was prepared from WFI (water for injection), GuHCl salt and EDTA. The pH of the 4.6 M GuHCl solution was adjusted to pH 7.2 to 7.4 with NaOH.

1.7 M Guanidine Hydrochloride

The 1.7 M GuHCl solution with 1 mM EDTA (Titriplex) was prepared from WFI (water for injection), GuHCl salt and EDTA. The pH of the 1.7 M GuHCl solution was adjusted to pH 7.2 to 7.4 with NaOH.

10 mM NaCl Diafiltration Solution

The diafiltration solution was prepared from WFI and NaCl. The conductivity of the diafiltration solution was determined at 1.0 to 1.2 mS/cm.

Experimental Procedures

Solubilisation of Apo A-I Precipitate

Apo A-I precipitate was dissolved in 4.6 M guanidine hydrochloride (GuHCl), homogenized, and the pH adjusted to pH 7.3±0.1.

Clarifying Filtration

The filtration solution was clarified by depth filtration to remove residual filter aid. The filter was prewashed with water for injection (WFI) and post-washed with 4.6 M GuHCl solution. The post-wash is combined with the filtrate, achieving a GuHCl concentration in the filtrate of about 3.5 M. The combined filtrate was collected and had an Apo A-I concentration in the range of 0 to 30 g/L.

Before the virus filtration step, a heat treatment step was conducted to provide virus inactivation.

Heat Treatment

For the heat treatment, the pH was adjusted to 7.1 to 7.5. The GuHCl concentration was calculated according to the following formula and adjusted to at least 3.0 M.

$$\text{GuHCl[M]} = -41.4 - (0.0170 \times \text{Protein[g/L]}) + (41.5 \times \text{Density[g/cm3]})$$

The mixture was then incubated at a temperature of about 60.0° C. for about 30 minutes to about 4 hours. The mixture was returned to room temperature and diluted before being subjected to the virus filtration step.

Dilution Step

Prior to the virus filtration step, the mixture was diluted with WFI to a final GuHCl concentration of 1.5-2.0 M and an Apo A-I concentration in the range of 0 to 30 g/L.

Virus Filtration

The purpose of the virus filtration step was to physically remove virus particles.

The prefiltration was conducted using a PALL SKL 7002 NTP 0.1 μm (Nylon). Then a sterile Planova BioEx nanofilter (Asahi Kasei Corporation) with 1 m$^2$ filter area was used for the filtration step. The BioEx filter allowed at least 340 kg of solution per m$^2$ of filter surface area. Both pre-filter and virus-removing filter were flushed at room temperature with 1.7 M GuHCl. The dead-end virus filtration process was performed at room temperature. The pressure was maintained below 3.4 bar. After completion of the filtration, the filter was post-flushed with 1.7 M GuHCl. Recovery of Apo A-I across the step is excellent with values above 95% and typically around 100%.

Example 2

Figure 2:
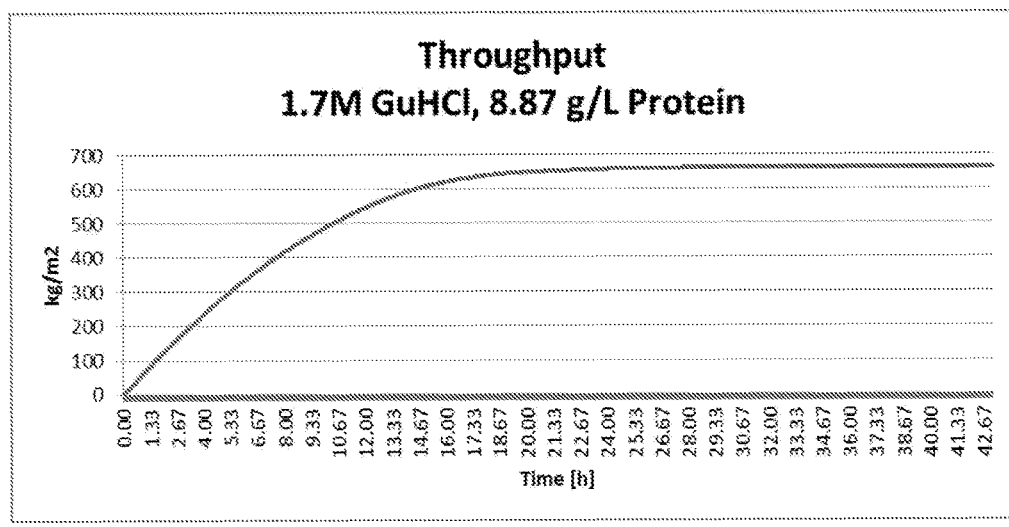
FIG. 2: showing through-put of the solution [kg/m$^2$] during nanofiltration with conditions of 1.7M GuHCl, 8.9 g/L Protein.
Figure 3:
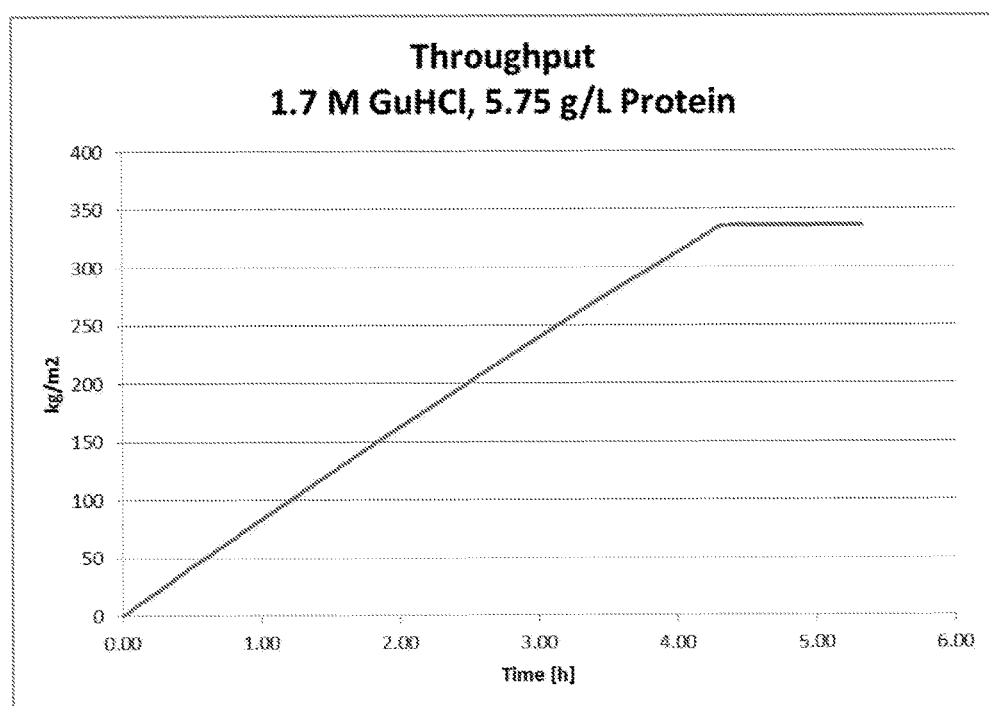
FIG. 3: showing through-put of the solution [kg/m$^2$] during nanofiltration with conditions of 1.7M GuHCl, 5.8 g/L Protein.
Figure 4:
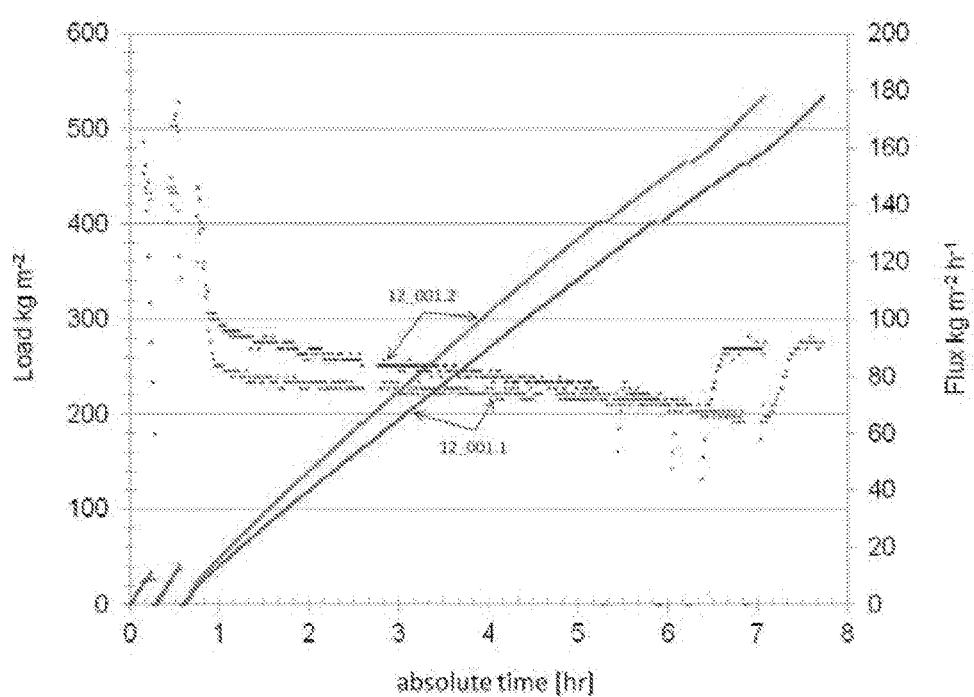
FIG. 4: showing the load and flux throughout the nanofiltration.

A comparison of filtration using a BioEx filter in the presence of different GuHCl (1.7 M & 3.2 M) and Apo A-I concentrations (5.8, 8.9, 19.7 g/L) was conducted (FIGS. 1 to 3). The virus filtration processes were conducted in an analogous manner to that described above in Example 1.

Additional filtration studies demonstrated that lower concentrations of GuHCl (1.0 M & 1.3 M) could result in unstable solutions that caused filter blockage in this system. These results highlight the benefit of optimising GuHCl concentration levels to facilitate virus filtration.

Example 3

An Apo A-I sample was spiked with MVM at a ratio of 1:1000. The spiked sample was filtered at a protein concentration of 10 to 12 g/L through a Planova BioEX virus removal filter in dead end mode at a pressure of about 2.4 bar. Samples of the filtrate were removed and assayed for residual virus infectivity (Table 1). The results demonstrate complete virus retention was achieved across the GuHCl concentration range. The lower GuHCl concentrations resulted in increased MVM log reduction values (LRV).

TABLE 1

| GuHCl mol/L | Filtrate kg/m$^2$ | LRV Log TCID$_{50}$/ml ± s$_e$ |
|---|---|---|
| 2.0 | 460 | ≥4.3 |
| 2.5 | 422 | ≥4.0 |
| 3.0 | 502 | ≥3.9 |

TABLE 1-continued

| GuHCl mol/L | Filtrate kg/m$^2$ | LRV Log TCID$_{50}$/ml ± s$_e$ |
|---|---|---|
| 3.5 | 267 | ≥3.6 |
| 2.0 | 402 | ≥4.2 |
| 2.5 | 354 | ≥4.0 |
| 3.0 | 308 | ≥3.9 |
| 3.5 | 311 | ≥3.7 |

In a further virus filtration study conducted under similar conditions MVM virus breakthrough was observed in the presence of 3.4 M GuHCl. Hence concentrations below about 3.0 M GuHCl are thought to improve removal of viruses with a diameter of approximately 20 nm (e.g. parvoviruses) using virus removal filters (such as the BioEx) in the manufacture of Apo A-I preparations.

Example 4

The study was intended to determine the effectiveness of virus filtration in the manufacture of Apo A-I, to clear MVM from the starting material. MVM was used as a model virus for very robust, small non-enveloped viruses including B19V.

Study Design

An Apo A-I sample was spiked with MVM at a ratio of 1000:1. The spiked sample was filtered through a Planova BioEX virus removal filter. At different time points, samples of the filtrate were removed and assayed for residual virus infectivity.

When ≥115 g filtrate was collected, the test system was re-spiked with MVM at a ratio of 100:1. Filtration was then continued and stopped when ≥8 g filtrate was collected. The filtrate was assayed for residual virus infectivity. Finally, the filter was post-washed with at least 12 g of 1.7 mol/L GuHCl solution. The post-wash fraction was collected separately and also analyzed for virus infectivity.

In each experiment:
Cytotoxicity of the test systems was determined
Titer of virus stock was determined
Stability of the virus was determined
Interference was determined
Clearance was determined Evaluation of Cytotoxic Effects Cytotoxicity was assayed by a non-radioactive cell viability assay using virus free test system, serially diluted in cell-culture medium to determine eventual cytotoxic effects of the sample. Samples resulting in less than 60% proliferative activity of the positive control were considered cytotoxic.

Viral Interference Assay

Virus interference was performed by TCID50 end point titration utilizing the non-cytotoxic concentration of virus free test system for the serial dilution of the stock virus. Interference was assessed by direct comparison of the virus titers obtained in interference assays to the virus titers obtained in the standard TCID50 assays of stock virus performed in culture medium.

Virus Titer Determination (TCID50)

Virus titers were determined by TCID50 (tissue culture infectious dose 50%). Three fold serial dilutions of desalted samples were used. Viral infectivity was assayed by end-point titration on indicator cells in 96 well plates.

Bulk Analysis (BA)

BA was used to lower the detection limit of the virus determination assay. Viral infectivity was assayed by dispensing 9 ml of desalted samples each, corresponding to 3 ml of the original sample, onto two 96 well plates on indicator cells.

Data Processing

Calculation of virus titers determined by TCID50 on microtiter plates Virus titers and their errors were calculated using the method of Spearman & Karber (Excel Makro: kaerber3_111.xls). Input numbers were the results from the titer determination.

Calculation of Reduction Factors

The virus reduction factor (LRF) of the process was calculated according to "Virus validation studies: the design, contribution and interpretation of studies validating the inactivation and removal of viruses" (CPMP/BWP/268195/Final; 14 Feb. 1996) and the requirements of the Bundesgesundheitsamt and the Paul-Ehrlich-Institute, Bundesamt foir Sera und Impfstoffe (4. Mai 1994).

Results

Cytotoxicity

No cytotoxicity was observed in both lots of the virus-free test system.

Interference Assay

| Exp. Nr. | Log TCID$_{50}$/ml ± s$_e$ |
|---|---|
| 12_001.1 | 8.40 ± 0.12 |
| 12_001.2 | 8.40 ± 0.11 |

No interference was observed.

Bulk Analysis

Bulk analysis with 3 ml samples lowers the detection limit to ≤−0.0006 log TCID50/ml (95% confidential limit). All samples tested negative for infectious virus. Hence, complete removal of MVM was achieved throughout the filtrations in both experiments.

Discussion and Conclusions

The present study was intended to determine the effectiveness of virus filtration to clear MVM from the starting material. MVM was used as a model virus for very robust, small non-enveloped viruses and B19V.

Complete clearance of MVM by the Planova BioEX virus removal filter was observed, yielding a mean LRF of ≥6.21±0.11. No cytotoxicity of the test system and no interference with viral-infectivity were observed.

Example 5

To examine the effect of the heat treatment step on Apo A-I solutions (as described in Example 1, Heat treatment subsection) was heated to 60±1° C. and spiked with MVM at a ratio of 100:1.

The spiked test system was kept at that temperature for 3 hours. Samples were collected at different time points and analyzed for virus infectivity to monitor virus reduction and inactivation kinetics throughout the process.

A sample of the test system was warmed up to 60±1° C. and kept at this temperature throughout the whole experiment. The temperature was monitored and recorded during the experiment. After having reached the target temperature, the test system was spiked with 0.1 µm filtered MVM at a ratio of 100:1. Sample 1 was taken immediately after spiking. Additional samples were taken after 1, 5, 10, 15, 30, 60, 120 and 180 minutes. All samples were diluted 1:10 with ice cold cell culture medium and stored on ice until further processing. Then, 1 ml of the diluted sample was passed through a PD-10 size exclusion column (GE Healthcare) in order to remove GuHCl. Briefly, 1 ml sample was applied to a column, the flow through was discarded. Then, the column was rinsed with 1 ml of PBS, the flow through was discarded. Finally, 3 ml of PBS were applied to the column and the desalted fraction was collected in a volume of 3 ml; resulting in another 1 to 3 dilution. Then, the virus titer in the desalted samples was determined by end point titration (TCID50). Additional samples were taken at 30, 60, 120 and 180 minutes for bulk analysis (BA) and stored on ice until further processing. From each sample three times 1 ml were desalted as described before. In total, 9 ml of the desalted fractions were collected. The following parameters were determined as per the methods described above in Example 4:

Cytotoxicity of the test systems
Titer of virus stock
Interference
Clearance

No cytotoxicity and no interference with viral infectivity were observed with all tested samples. Rapid inactivation kinetics with complete inactivation of MVM within 30 minutes was observed. The obtained mean LRF of ≥6.03±0.12 log indicates efficient clearance of MVM during heat treatment at 60° C. within 30 minutes.

Example 6

The studies were intended to determine the effectiveness of the two dedicated virus reduction steps—filtration and heat treatment steps to clear virus from Apo A-I solutions. The manufacturing process scheme followed is as described in Example 1 and the spiking studies were conducted in an analogous manner as to that described in Example 4 (virus filtration) and Example 5 (heat treatment). The studies demonstrated the following levels of virus reduction:

|  | Virus filtration (LRV) | Heat treatment (LRV) | Combined (LRV) |
| --- | --- | --- | --- |
| MVM (parvovirus) | ≥6.21 ± 0.11 | ≥6.03 ± 0.12 | ≥12.24 ± 0.23 |
| EMCV (Picornavirus, Hepatitis A) | ≥4.69 ± 0.14 | ≥4.75 ± 0.12 | ≥9.44 ± 0.26 |
| BVDV (Flaviviridae, Hepatitis C) | ≥4.27 ± 0.17 | ≥4.69 ± 0.13 | ≥8.96 ± 0.3 |

Thus the methods of the present invention enable Apo A-I to be manufactured with at least 12 log LRV for parvoviruses like MVM, at least 9 log LRV for non-enveloped viruses like EMCV, and at least 8.5 log LRV for lipid enveloped viruses like BVDV.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention claimed is:

1. A method for purifying apolipoprotein A-I (Apo A-I) to remove viruses, comprising filtering a solution comprising Apo A-I and guanidine hydrochloride (GuHCl) through a filter having a pore size of from 15 nm to 35 nm, wherein the solution subject to filtration comprises Apo A-I at a concentration of from 5 to 30 g/L and GuHCl at a concentration of from 1.5 to 3.2 M.

2. The method of claim 1, wherein the pH of the solution subject to filtration is from 7.1 to 7.5.

3. The method of claim 1, wherein the filtering is performed at a pressure of from 0.2 to 3.4 bar.

4. The method of claim 1, wherein the filtering is performed at a temperature of from 18 to 26° C.

5. The method of claim 1, further comprising preparing the solution subject to filtration by (a) preparing a suspension of Apo A-I in 4.0 to 4.6 M GuHCl and (b) diluting the suspension to an Apo A-I concentration of from 5 to 30 g/L and to a GuHCl concentration of from 1.5 M to 3.2 M.

6. The method of claim 1, further comprising, before or after the filtering, subjecting the solution comprising Apo A-I and GuHCl to a heat treatment for virus inactivation.

7. The method of claim 6, wherein the solution subject to the heat treatment has a pH of from 6.6 to 8.0.

8. The method of claim 7, wherein the heat treatment comprises heating the solution at a temperature of from 55 to 61° C. for a period of time period of from 30 minutes ±3minutes to 4 hours ±24 minutes.

9. The method of claim 8, wherein the solution subject to heat treatment has a pH of from 6.6 to 8.0 and comprises GuHCl at a concentration of from 2.7 M to 3.9 M.

10. The method of claim 9, wherein the solution subject to the heat treatment has a pH of from 7.0 to 8.0.

11. The method according to claim 7, further comprising preparing the solution subject to the heat treatment that has a pH of from 6.6 to 8.0 by (a) preparing a suspension of Apo A-I in 4.0 to 4.6 M GuHCl and (b) adjusting the GuHCl concentration to be from 2.7 M to 3.9 M and the pH to be from 6.6 to 8.0.

12. The method of claim 1, wherein the filtering is performed by dead-end filtration.

13. A method of producing a reconstituted HDL formulation comprising purifying Apo A-I by the method of claim 1 and combining the purified Apo A-I with a lipid.

* * * * *